United States Patent
Henderson et al.

(10) Patent No.: US 11,598,723 B2
(45) Date of Patent: Mar. 7, 2023

(54) NDIR SENSOR, SAMPLING METHOD AND SYSTEM FOR BREATH ANALYSIS

(71) Applicant: Amphenol Thermometrics, Inc., Saint Marys, PA (US)

(72) Inventors: David Henderson, Goleta, CA (US); Andrian Kouznetsov, Santa Barbara, CA (US); James Sciaini, Santa Barbara, CA (US)

(73) Assignee: AMPHENOL THERMOMETRICS, INC., Saint Marys, PA (US)

( * ) Notice: Subject to any disclaimer, the term of this patent is extended or adjusted under 35 U.S.C. 154(b) by 214 days.

(21) Appl. No.: 16/653,585

(22) Filed: Oct. 15, 2019

(65) Prior Publication Data

US 2020/0116632 A1    Apr. 16, 2020

Related U.S. Application Data

(60) Provisional application No. 62/745,088, filed on Oct. 12, 2018.

(51) Int. Cl.
*G01N 21/61* (2006.01)
*G01N 33/497* (2006.01)

(52) U.S. Cl.
CPC ........... *G01N 21/61* (2013.01); *G01N 33/497* (2013.01)

(58) Field of Classification Search
CPC .. G01N 21/3504; G01N 33/497; G01N 21/61; G01N 33/004
See application file for complete search history.

(56) References Cited

U.S. PATENT DOCUMENTS

| | | | | |
|---|---|---|---|---|
| 3,539,803 | A | * | 11/1970 | Beerman ................ G01J 5/34 374/177 |
| 3,861,809 | A | | 1/1975 | Hall, Jr. |
| 4,292,978 | A | | 10/1981 | Guth |
| 4,859,858 | A | | 8/1989 | Knodle et al. |
| 4,859,859 | A | | 8/1989 | Knodle et al. |
| 5,092,342 | A | * | 3/1992 | Hattendorff ......... A61B 5/0836 250/343 |

(Continued)

FOREIGN PATENT DOCUMENTS

| | | |
|---|---|---|
| WO | WO-2017/180605 A1 | 10/2017 |
| WO | WO-2017/189546 A1 | 11/2017 |

OTHER PUBLICATIONS

T. A. Vincent, et al., "Development of a Low-Cost NDIR System for PPM Detection of Carbon Dioxide in Exhaled Breath Analysis", Science Direct, Procedia Engineering, vol. 120, 2015, pp. 388-391.

(Continued)

*Primary Examiner* — David A. Rogers
(74) *Attorney, Agent, or Firm* — Cantor Colburn LLP (57) ABSTRACT

A gas sensor has a light detector, a gas-tight support structure enclosing the light detector, a window positioned in said support structure, and a light source mounted to the support structure. A sample area is positioned in the support structure to receive a gas to be tested. The light source is aligned with the window, sample area, and the light detector to pass light from the light source through the gas in the sample area to the light detector. The sensor can be provided in a breadth sampling apparatus that has deflects gas to a bypass route so that only a portion of gas reaches the sensor.

20 Claims, 3 Drawing Sheets

(56) References Cited

U.S. PATENT DOCUMENTS

| | | | |
|---|---|---|---|
| 5,146,092 A | 9/1992 | Apperson et al. | |
| 5,341,214 A | 8/1994 | Wong | |
| 5,436,457 A | 6/1995 | Tomita | |
| 5,464,982 A | 11/1995 | Drucker et al. | |
| 5,468,961 A | 11/1995 | Gradon et al. | |
| 5,721,430 A * | 2/1998 | Wong | G01N 21/3518 250/338.5 |
| 5,739,412 A | 4/1998 | Stock et al. | |
| 5,739,535 A | 4/1998 | Koch et al. | |
| 5,793,044 A | 8/1998 | Mace et al. | |
| 5,834,777 A | 11/1998 | Wong | |
| 6,191,421 B1 | 2/2001 | Yamamori et al. | |
| 6,255,653 B1 | 7/2001 | Kouznetsov | |
| 6,326,611 B1 * | 12/2001 | Kennedy | H01L 27/14618 250/343 |
| 6,410,918 B1 | 6/2002 | Kouznetsov | |
| 6,599,253 B1 | 7/2003 | Baum et al. | |
| 6,632,402 B2 | 10/2003 | Blazewicz et al. | |
| 6,656,127 B1 | 12/2003 | Ben-Oren et al. | |
| 6,888,101 B2 * | 5/2005 | Davis | A61B 5/083 128/200.24 |
| 6,955,650 B2 | 10/2005 | Mault et al. | |
| 6,955,652 B1 | 10/2005 | Baum et al. | |
| 6,969,857 B2 | 11/2005 | Owen | |
| 7,285,782 B2 * | 10/2007 | Schubert | G01N 21/09 250/339.13 |
| 7,301,125 B2 * | 11/2007 | Davis | A61B 5/083 219/201 |
| 7,408,158 B1 | 8/2008 | Mengel et al. | |
| 7,479,635 B2 * | 1/2009 | Ichikawa | G01J 5/045 250/338.1 |
| 7,659,504 B1 * | 2/2010 | Rich | G01N 21/3504 250/239 |
| 7,833,480 B2 | 11/2010 | Blazewicz et al. | |
| 8,459,261 B2 | 6/2013 | Ricciardelli et al. | |
| 8,460,203 B2 | 6/2013 | Ricciardelli | |
| 8,482,723 B2 | 7/2013 | Tsukii et al. | |
| 8,695,402 B2 * | 4/2014 | Thorson | G01N 21/1702 73/24.02 |
| 9,103,818 B2 | 8/2015 | Son | |
| 9,285,251 B2 * | 3/2016 | Enquist | G01N 21/783 |
| 9,562,890 B2 | 2/2017 | Son | |
| 9,562,915 B2 | 2/2017 | Burgi et al. | |
| 9,581,539 B2 | 2/2017 | Brugnoli | |
| 9,820,656 B2 | 11/2017 | Olivier | |
| 10,012,585 B2 | 7/2018 | Goldring et al. | |
| 10,113,957 B1 | 10/2018 | Yi et al. | |
| 10,359,417 B2 | 7/2019 | Hammarlund et al. | |
| 10,495,552 B2 | 12/2019 | Cooper et al. | |
| 10,539,500 B2 * | 1/2020 | Jones | G02B 1/02 |
| 10,682,072 B2 | 6/2020 | Ratto et al. | |
| 10,794,768 B2 * | 10/2020 | Simon | G01J 5/0225 |
| 10,845,047 B2 * | 11/2020 | Biermann | G01J 1/4228 |
| 10,898,108 B2 | 1/2021 | Stambeck | |
| 11,079,321 B2 | 8/2021 | Castagna et al. | |
| 2001/0048079 A1 | 12/2001 | Brunamoti et al. | |
| 2003/0205670 A1 | 11/2003 | Shibayama | |
| 2004/0206906 A1 | 10/2004 | Owen | |
| 2005/0230624 A1 | 10/2005 | Schubert | |
| 2005/0245836 A1 | 11/2005 | Star et al. | |
| 2006/0060788 A1 * | 3/2006 | Uchida | G01J 5/12 250/343 |
| 2007/0093725 A1 | 4/2007 | Shaw | |
| 2008/0299670 A1 | 12/2008 | Smeets et al. | |
| 2011/0088446 A1 | 4/2011 | Son | |
| 2011/0109905 A1 | 5/2011 | Martin | |
| 2012/0165694 A1 | 6/2012 | Meka et al. | |
| 2012/0291517 A1 | 11/2012 | Son | |
| 2013/0023782 A1 * | 1/2013 | Karlsson | G01J 3/42 600/532 |
| 2013/0253336 A1 | 9/2013 | Haveri | |
| 2013/0305808 A1 | 11/2013 | Yoo | |
| 2014/0250975 A1 | 9/2014 | Kane | |
| 2014/0268157 A1 * | 9/2014 | Bogoev | G01N 21/15 356/437 |
| 2015/0192517 A1 * | 7/2015 | Andre | G01N 21/031 250/343 |
| 2015/0377781 A1 | 12/2015 | Lewis et al. | |
| 2016/0054296 A1 | 2/2016 | Son | |
| 2017/0038294 A1 | 2/2017 | Kshirsagar et al. | |
| 2017/0097301 A1 | 4/2017 | Lefebvre et al. | |
| 2017/0100057 A1 | 4/2017 | Wang | |
| 2017/0284905 A1 | 10/2017 | Krauss et al. | |
| 2017/0299484 A1 | 10/2017 | Brüchig et al. | |
| 2018/0235480 A1 | 8/2018 | Olivier | |
| 2018/0321207 A1 | 11/2018 | Hellgren et al. | |
| 2018/0348021 A1 * | 12/2018 | Ziems | G01J 5/0014 |
| 2019/0381263 A1 | 12/2019 | Siska et al. | |
| 2020/0093399 A1 | 3/2020 | Miller | |
| 2021/0307642 A1 | 10/2021 | Candell et al. | |

OTHER PUBLICATIONS

CAPNOSTAT Mainstream CO₂ Sensor Connect & go. Breathe easier. Cutting Edge CO₂ Technology for Patients in the ICU, OR and EMS Applications, www.oem.respironics.com, 2017, 1 pg.

CAPNOSTAT Mainstream CO₂ Sensor, Cutting Edge CO₂ Technology for Patients in the ICU, OR and EMS Applications, www.oem.respironics.com, 2 pgs.

Telaire, T6617 High Concentration Sensor Module, Compact CO₂ Module Designed to Integrate into Existing Controls and Equipment, www.telaire.com, 2014, 3 pgs.

International Search Report & Written Opinion for PCT/US19/56243, dated Mar. 10, 2020, 10 pgs.

Telaire, T3000 Series CO₂ Sensors for Harsh Environments; Amphenol Sensors; www.telaire.com; 2018; 4 pgs.

Supplementary European Search Report for European Application No. 19870882 dated May 16, 2022, 7 pages.

Kim et al., "NDIR Ethanol Gas Sensor with Two Elliptical Optical Structures", ScienceDirect, Procedia Engineering 168, 2016, pp. 359-362, 30th Eurosensors Conference, EUROSENSORS 2016.

* cited by examiner

NDIR SENSOR, SAMPLING METHOD AND SYSTEM FOR BREATH ANALYSIS

RELATED APPLICATIONS

This application claims the benefit of U.S. Provisional Application No. 62/745,088, filed Oct. 12, 2018, the entire contents of which are incorporated herein by reference.

BACKGROUND OF THE DISCLOSURE

Field of the Disclosure

The present disclosure relates to sensors. More particularly, the present disclosure relates to an NDIR sensor for breath analysis.

BACKGROUND OF THE RELATED ART

A Nondispersive Infrared (NDIR) sensor measures absorption of IR (infrared) light within narrow wavelength range between the source and the detector due to presence of the gas of interest. The higher the gas concentration, the higher the absorption and the lower is the signal detected by IR detectors. This method has been used before including in a variety of commercial products. For example, Amphenol Advanced Sensors manufactures is a high concentration CO2 sensor, model T6617. This sensor however does not have fast response time and features that make it applicable for real time breath monitoring.

In addition, Capnostat offers a sensor used for breath measurements. The gas is sampled via mainstream sampling where the entire breath passes through a sample cell. This sample cell has a piece of replaceable plastic as it may become dirty over time. High power consumption, long warm up time, narrow operating temperature range, need for periodic recalibration and need for disposable replaceable parts makes it not ideal for portable measurements and consumer level applications.

These designs employ much more power consuming components (heaters) and disposable element (water traps and sampling tubes), to deal with water condensation.

SUMMARY OF THE DISCLOSURE

A gas sensor has a light detector, a gas-tight support structure enclosing the light detector, a window positioned in said support structure, and a light source mounted to the support structure. A sample area is positioned in the support structure to receive a gas to be tested. The light source is aligned with the window, sample area, and the light detector to pass light from the light source through the gas in the sample area to the light detector. The sensor can be provided in a breadth sampling apparatus that has deflects gas to a bypass route so that only a portion of gas reaches the sensor.

DETAILED DESCRIPTION OF THE PREFERRED EMBODIMENTS

In describing the illustrative, non-limiting preferred embodiments of the disclosure illustrated in the drawings, specific terminology will be resorted to for the sake of clarity. However, the disclosure is not intended to be limited to the specific terms so selected, and it is to be understood that each specific term includes all technical equivalents that operate in similar manner to accomplish a similar purpose. Several preferred embodiments of the disclosure are described for illustrative purposes, it being understood that the disclosure may be embodied in other forms not specifically shown in the drawings.

Figure 1:
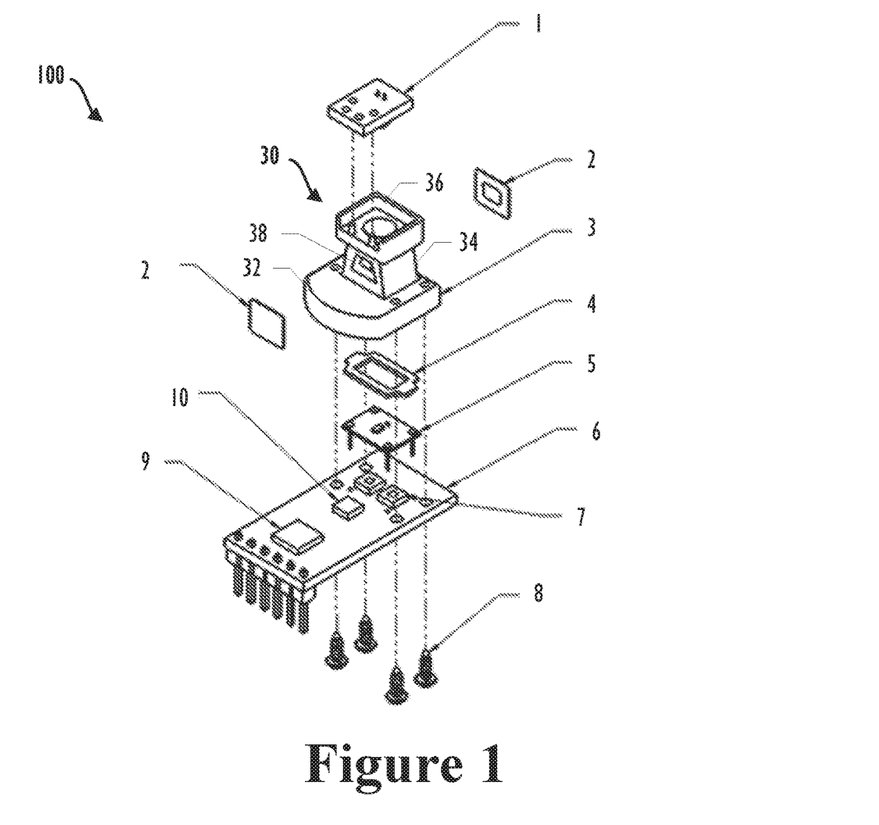
FIG. 1 is a perspective exploded view of a sensor in accordance with an embodiment of the disclosure.
Figure 3A:
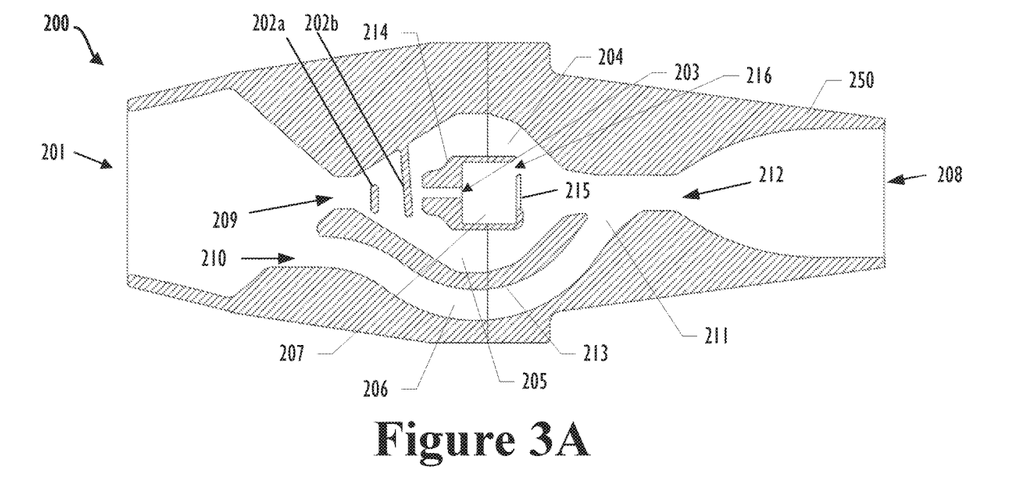
FIG. 3A is a cross-sectional view taken along lines A-A of FIG. 3C showing an example breadth sampling system using the gas sensor assembly of FIG. 1.
Figure 3B:
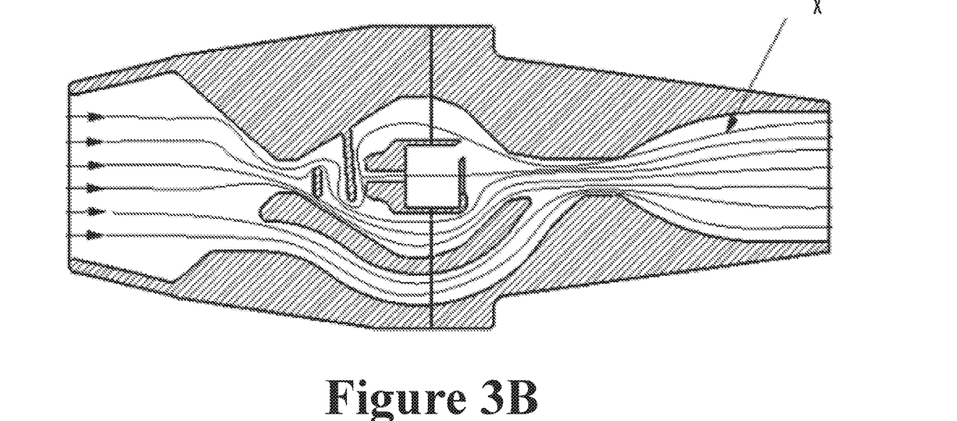
FIG. 3B shows air flow through the system of FIG. 3A.
Figure 3C:
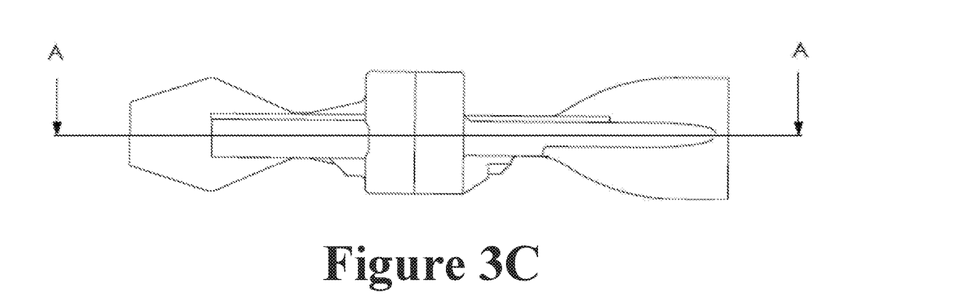
FIG. 3C is a side view of the breadth sampling system.
Figure 3D:
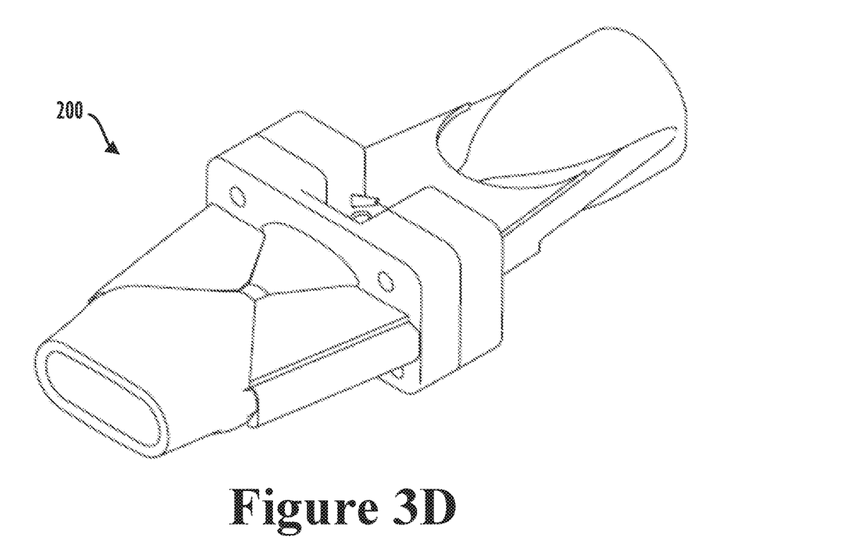
FIG. 3D is a perspective view of the breadth sampling system.
Figure 4:
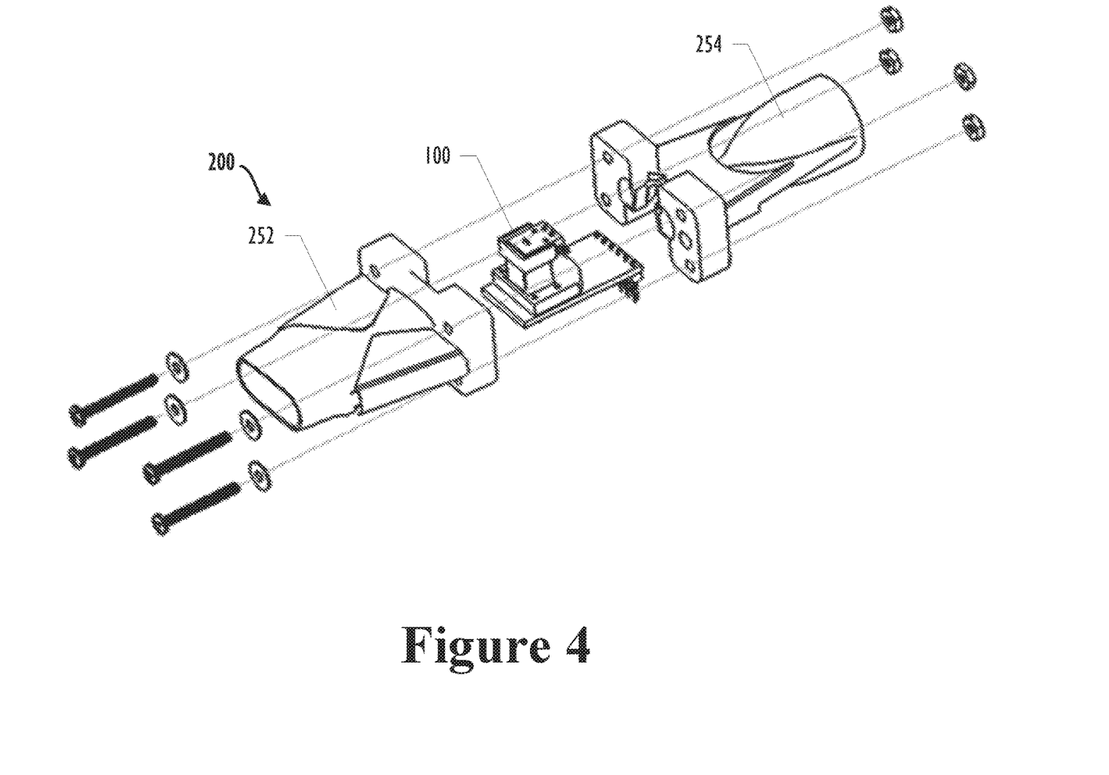
FIG. 4 is a perspective exploded view of the breadth sampling system and gas sensor assembly.

Turning to the drawings, a Nondispersive Infrared (NDIR) gas sensor assembly 100 is shown in FIG. 1. The NDIR sensor 100 can be combined with a sampling system 200, as shown in FIGS. 3-4. A hydrophilic, heated, or unheated optical window assembly 5 is placed inside an NDIR sensor measuring chamber to eliminate effects of condensation that may happened due to high moisture content in exhaled air. The design has a wide temperature range due to the synergy of various features working together to not have condensation problems even at cold temperatures.

The sensor assembly 100 includes a support 6, detectors 7, a window assembly 5, and an optical bench assembly 3. In the non-limiting example embodiment shown, the support 6 is a flat substrate that is planar and can have, for example, a generally square or rectangular shape. The support 6 has a first side forming a top surface and a second side forming a bottom surface, the first side opposite the second side. In one embodiment, the support 6 can be a Printed Circuit Board Assembly (PCBA). The support 6 forms a mechanical base that retains both electrical and mechanical components. The electrical components of the PCBA 6 typically include the detector (for example, an infrared (IR) detector) 7, controller or microprocessor 9 and signal conditioning devices 10, such as for example a voltage regulator to regulate the input voltage, IR source driver circuit to modulate the IR source, a detector amplifier circuit to give the IR signal gain, analog to digital converter for measurement, and microprocessor or ASIC type integrated chip.

The detector 7 is mounted on the top surface of the PCBA 6. Any suitable number of detectors 7 can be provided, and in the embodiment shown there are two detectors mounted to the PCBA 6 side by side. The detector 7 can be an infrared detector, such as for example photodiodes, pyroelectric, and thermopile detectors. The detectors 7 can have bandpass filters that detect energy in precise wavelengths. For example, $CO_2$ detection filters are often designed for wavelength of 4.26+/−0.1 micron. A second reference detector has central wavelength of 3.9+/−0.1 micron.

Figure 2:
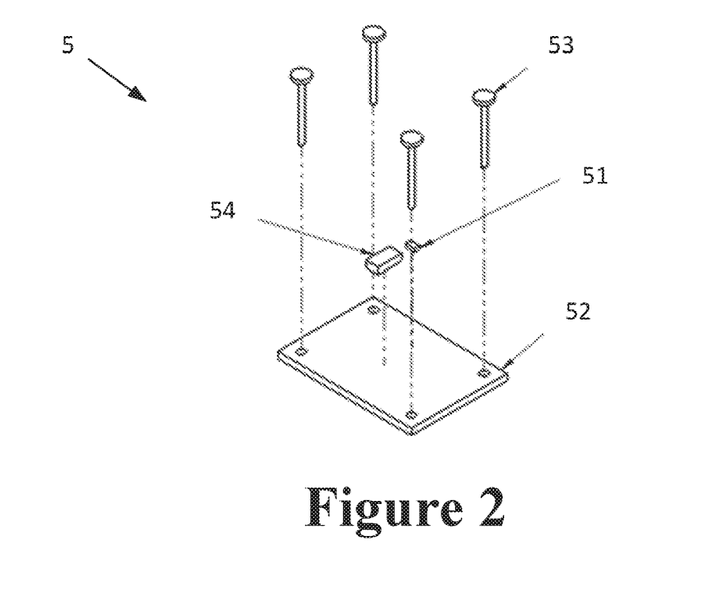
FIG. 2 is a perspective exploded view of the window used in FIG. 1.

FIG. 2 is a detailed view of the optical window assembly 5. The window assembly 5 has an optically transparent in IR (infrared) wavelengths window 52, heater 54 and temperature sensor 51. The window 52 is flat and planar with a first side having a top surface and a second side having a bottom surface, and can have the general shape of a square or rectangle, though other suitable shapes can be utilized. The window assembly 5 is mounted over the one or more detectors 7, and the window 52 is sized to fit over and fully cover the one or more detectors 7.

The window 52 serves as a protection for the detectors 7 against thermal shock that happens during exhalation (especially if the breath test is taken outside in cold conditions) and from moisture in exhaled air that reaches condensing levels. Both thermal shock and condensing moisture could otherwise prevent the detectors 7 from accurately measuring radiation absorption by $CO_2$ gas and consequentially measuring $CO_2$ gas concentration. There is no seal between the window 52 and the PCBA 6, but a gasket seal 4 is provided between the Optical Bench Assembly (OBA) 3 and the window assembly 5. This seal (gasket is optional depending on specific design) 4 prevents exhaled air getting underneath the window 5 into the area where the detectors 7 are located. This effectively isolates the detectors 4 from exhaled air.

The window 52 has hydrophobic or hydrophilic properties, for example the window 52 can have a Titanium Dioxide or other hydrophilic coating on one or both sides of the window 52. In most of conditions, the coating is sufficient to reduce the effect of possible condensation of water from exhaled air inside the measuring chamber. The hydrophilic coating reduces effects of condensation that may occur even with gas flow carefully controlled. The window 52 can have hydrophobic coating, anti-reflection coating (anti-reflection coating can also be hydrophilic or hydrophobic), or no coating. The window 52 itself can be made of any suitable material that is transparent in the wavelength range of interest, in the preferred embodiment it is 3 to 5 microns range.

Referring to FIGS. 1, 2, the heating element 54 and temperature sensor 51 can be mounted to the top surface of the window 52 and/or the bottom surface of the window 52. The heating element 54 (for example, a resistor) accommodates broad temperature ranges, so the sensor 100 can operate in environmental temperatures close to freezing. The heating element 54 heats the window 52, and not the entire sensor assembly 100, which allows for extremely fast warm-up and low power consumption. The heater 54 heats the window 52.

The air that has a lot of moisture does not reach the detectors 7 due to seal formed between OBA 3 and the window 52 by the seal 3 and 4. However, unwanted condensation can happen on the outer surface of the window 52 (that faces up in FIG. 1). To prevent this condensation, the heater 54 heats the window 52 to temperatures that are necessary to eliminate condensation (e.g., at least 33 degrees C.). Depending on intended use of the analyzer, the heater 54 may not be necessary (when the analyzer is used indoors only for example). Due to small size, high temperature conductivity of the window 52 and sufficient heating power, the window 52 can be heated within seconds time frame (e.g., 2-10 seconds). A measurement can be taken and then the heater 54 turned off until the next measurement. Because only the window 52 is heated, and because the window 52 can be intermittently heated, significant power is saved and allows long operation on a battery.

The heater 54 and sensor 51 are electrically or wirelessly connected to the microprocessor 9. The temperature sensing element 51 (for example a thermistor) provides window temperature measurements to the microprocessor 9, which can then control operation of the heating element 54. The window assembly 5 has a gasket 4 which is compressed between the top surface of the window 52 and the optical bench assembly (OBA) 3. The gasket 4 extends around the outer perimeter of the window 52 and has a central opening for the sensor 51 and heater 54.

The window 5 can have different options depending on an application. In the non-limiting example embodiment shown in FIG. 2, the window 52 is a flat square or rectangular panel or member that is made out of a material (such as for example sapphire) that is transparent in IR wavelength range of interest. An electrical printed circuit for heating resistor 54 heats the window 52, and a thermistor 51 senses the temperature to control the temperature of the window 52 by the microcontroller 9 (FIG. 1). The conductive pins 53 mount the window 52 to the PCBA 6 (FIG. 1) and at the same time provide necessary electrical connections (with any necessary lead lines) for the heating resistor 54 and the thermistor 51. In one embodiment, the window 52 is soldered to the pin heads 53, and the pins 53 are soldered to the PCBA 6. The window 52 is not floating over the detectors 7, but is secured to the PCBA 6 above the detectors 7. Other suitable configurations can be provided, for example the window 52 can rest on the detectors 7 being pressed from the top by the gasket 4 (if electrical connections (heater 54) is not needed).

In other embodiments, the window 52 can be made out of silicon, or other optically transparent in IR material including plastic, polymer materials. The window may have anti-reflective coating to enhance its optical properties. The window may have hydrophilic coating (like Titanium Dioxide) or hydrophobic coatings to help dealing with possible condensation. It is also possible having a coating that serves both purposes—as antireflective coating and hydrophilic coating (or hydrophobic coating) at the same time. Titanium Dioxide is one of the materials that can be used as both antireflective and hydrophilic coating.

Returning to FIG. 1, the optical bench assembly (OBA) 3 is a structural support that retains a light or optical source 1, such as an infrared source, and aligns the IR source 1 with the gas to be detected and the light or optical detectors 7, such as infrared detectors. The OBA 3 is mounted to the PCBA 6, such as by one or more fasteners such as screws 8, or alternatively adhesives or plastic with snap features or adhesive or a combination of these methods. The OBA 3 encloses at least the detectors 7 and window assembly 5, and can also enclose the signal conditioning device 10 and/or microprocessor 9. The OBA 3 is optionally built with carbon fiber loaded ABS to provide an EMC shield for sensitive components of signal conditioning and data acquisition path including the IR detectors 7 and the signal conditioning device 10. Alternatively, the OBA 3 can be built with metallized plastic, or metal. Regular ABS or similar plastic with no metal coating or carbon filling may also be used. This may be possible when the sensor is used in the applications with less demanding EMC requirements. In addition, the OBA 3 may include reflective surfaces to improve optical radiation propagation form the IR source 1 to IR detectors 7. These reflective surfaces may include entire OBA interior, and or specially arranged reflectors.

In the example embodiment of FIG. 1, the OBA 3 is a housing structure that extends over the detectors 7, as well as the window assembly 5, and the signal conditioning device 10. The OBA 3 is a single piece member or body 30 that includes a base portion 32, a middle portion 34, and a head portion 36. The base portion 32 cooperates with the PCB 6 to form an enclosure that shields the sensitive components (i.e., IR detectors 7 (there two of them) and signal conditioning device 10). That provides a high level of resistance to ElectroMagnetic Interference (EMI). The base portion 32 has a flat platform and one or more sides or side walls that extend downward from the flat platform. The distal edges of the side walls contact the top surface of the PCBA 6 and form a gas-tight and moisture-tight seal therebetween to provide a gas- and/or water-tight enclosure around the IR detectors 7. The seal between the PCBA 6 and the base portion 32 is gas tight in the area of the gasket 4, to isolate gas of interest in the specific area of the OBA, and it is moisture tight to prevent moisture collection underneath the window 52 so that it holds small amounts of condensate that will be evaporated by the heater 54. The base 32 defines an interior space between the flat platform, side walls, and the top surface of the PCBA 6, and the components (detectors 7, signal condition device 10, window assembly 5) are received in that interior space.

The flat platform has an opening that is aligned with the window 52 and the IR detectors 7. The middle portion 34 of the body 30 extends upward (in the embodiment of FIG. 1) about the opening of the flat platform. The middle portion 34 has four sides or side walls, and a central space or gas sample area. Openings 38 are positioned on one or more, and here shown as two opposing sides, of the OBA 3 middle portion. The gas sample can pass through the openings and into the central space. Diffusion hydrophobic filters 2 cover the openings 38, and allow the gas sample to pass while preventing dust and water droplets from entering into the central space of the middle portion 34.

The top or head portion 36 of the OBA 3 is positioned at the top of the middle portion. The head 36 has a flat platform, and upwardly-extending side walls. The flat platform has an opening that is aligned with the middle portion 34. A flat PCBA is positioned at the top of the head portion and forms a cover. The PCBA has an infrared emitting source 1 that is modulated by the microcontroller 9 and driving circuit. Sources suitable to mount to this PCB are miniature tungsten filament lamp assemblies, MEMS based IR sources, and LEDs that emit energy in the wavelengths of interest. The IR source PCB can be removably secured to the head portion 36, for example the IR source PCB can be received in channels or slots formed at the upper inside of the side walls of the head 36.

Thus, the body 30 is configured to provide a continuous linear path for light to travel uninterrupted from the IR source 1 at the head portion 36, through the opening in the head platform, through the central space at the middle portion 34 where it comes into contact with the gas being sampled, through the opening in the base 32 flat platform, then through the window assembly 5, to the detector 7 enclosed by the base portion 32. The middle portion 34 allows gas to enter the OBA 3, but filters 2 prevent dust, water droplets and other contaminants from entering the OBA 3 and otherwise interfering with the measurement. The window assembly 5 covers the opening at the bottom of the middle portion 34 in the flat platform of the base portion 32, and seals the central space of the middle portion 34 from the base 32. The window 5 and gasket 4 prevent gas or other elements from passing into the base portion and the interior space of the base portion where the IR detector 7 and signal conditioning device 10 are located, while allowing the IR signal to pass uninterrupted from the IR source 1 to the IR detector 7. The volume between the IR source 1 and the window 5 as well as OBA walls form the sampling chamber where $CO_2$ concentration is measured using typical NDIR method. The heater 54 and the thermistor 51 are located in the middle between the two detectors 7, so that they do not obscure the optical signal.

The window 5 also protects sensitive IR detectors 7 and electronics from thermal shock happening when the sensor starts to operate and warm (not conditioned) gas (interchangeably referred to here as "air") enters the sensor. In addition, the window 5 prevents moisture from entering the area where detectors and electronics are located. And, the window 5 prevents condensation on the window 5 surface due to high RH of exhaled air. And, the window 5 and gasket 4 prevent $CO_2$ from entering the space under the window, which is highly undesirable because trapped $CO_2$ could affect sensor response time and accuracy.

Breath Testing Devices

FIGS. 3, 4 show an example of a breadth or gas sampling system 200 in accordance with the present disclosure. As best shown in FIGS. 3A, 3B, 4, the breadth sampling system 200 has a body 250 that houses a sensor assembly, shown here as the sensor assembly 100 of FIGS. 1-2. However, any suitable sensor assembly can be utilized. The sensor assembly 100 and breadth sampling system 200 have separate utility and can be utilized independent of one another or together. That is, the sensor assembly 100 can be utilized with any breadth sampling system, and the breadth sampling system 200 can be utilized with any sensor assembly.

The sampling system 210 has an inlet 201, baffles 202, sensor inlet opening 203, bypass channels or routes 204, 205, 206, sensor area 207 for receiving the sensor 100, exhaust 208, inlet choke point 209, bypass inlet 210, bypass exhaust 211, and exhaust choke point 212. As shown in FIG. 4, the body 250 has a leading body portion 252 and a trailing body portion 254 and is configured to create the air flow X shown in FIG. 3B. In FIG. 4, the leading portion 252 and the trailing portion 254 are separate discrete bodies that are coupled together by fasteners or the like. Alternatively, the leading and trailing portions 252, 254 can be formed as a single integral one-piece housing. The sensor assembly 100 is situated substantially at the middle area of the body 250 at an intermediate body portion where the leading and trailing portions 252, 254 come together. The body 250 is substantially elongated and has a longitudinal axis that extends from the inlet 201 to the exhaust 208. The body 250 has a continuous internal central space that extends from the inlet 201 to the exhaust 208 between the side walls and top and bottom so that a gas can pass from the inlet 201 through the central opening to the exhaust 208. Similar design can be rearranged in not elongated but "folded", "wrapped", "twisted", and any other configuration, elongated being the simplest one.

The main inlet 201 is at the leading portion 252 of the body 250 and forms a mouthpiece that is shaped to match a person's mouth. That is, the mouthpiece forms an oblong elongated opening that is wider than it is tall so that the inlet 201 can easily and comfortably fit into the user's mouth. The inlet 201 has a receiving area defined by two sides, a top and a bottom. The sides taper sharply inwardly to form a choke point 209.

One or more (one shown) dividers or divider walls 213 can be provided at the choke point 209. The divider 213 is elongated and curved to create the bypass inlet 210, bypass route 206, and bypass exhaust 211. The divider 213 and bypass route 206 extend substantially parallel to the longitudinal axis of the body 250, and completely extend from the top to the bottom of the body 250. As shown, the bypass route 206 is formed between the divider 213 and one of the side walls, between the top and bottom of the body 250. The bypass route 206 has a first outward curve that gently curves outward toward the closer side wall (down in the embodiment of FIG. 3A) and away from a center of the body 250, and a second inward curve that curves sharply back inward toward the center of the body 250. The bypass route 206 extends from before the inlet side of the sensor receiving area 207 to after the outlet side of the sensor receiving area 207, so that gas traveling in the bypass route 206 is completely isolated from and bypasses the sensor 100 and the sensor receiving area 207.

The leading end face of the divider 213 creates two inlets, the bypass inlet 210 and the choke point inlet 209. The size of the respective inlets 210, 209, the shape and size of the bypass route 206, and the shape and size of the leading end face of the divider 213 can be adjusted to control the amount (volume) of gas that travels through the bypass route 206 and the amount (volume) of gas that travels through the choke point inlet 209.

Gas that passes through the choke point inlet 209 will enter the sensor receiving area. The one or more baffles 202 are located in the sensor receiving area. A first or leading baffle 202a is positioned right at the entry to the sensor receiving area behind the choke point 209, and the second or rear baffle 202b is positioned behind the first baffle 202a and just prior to the sensor opening 203 so there is a space between the opening 203 and the baffle 202b. The baffles 202 are shown as walls that can extend substantially transverse to the side walls and longitudinal axis. The baffles 202 can either be disconnected from the side wall, as shown by the first baffle 202a, or can be connected to at least one of the side walls, as shown with the second baffle 202b.

The baffles 202 operate to create a pressure differential that slows the travel of gas through the sensor receiving area and causes more gas to be directed from the intake receiving area into the bypass route 206. The rear baffle 202b does not completely block the sensor passage 203, and does not completely block the bypass passages 204, 205. Accordingly, the air circulates around there in an organized way, as shown in FIG. 3B. From the moment the person breathes in the inlet, the $CO_2$ levels and flow stabilize (FIG. 3B) inside the sensor and yet provide no condensation inside the sensor. The goal here is to bring minimum amount of exhaled air to the sensor chamber while assuring fastest response time possible. We need to bring 0.5 $cm^3$ samples of the exhaust air in the sensor chamber in a second time frame while the exhalation is happening.

A sensor housing or island 214 is positioned within the sensor receiving area and defines a first bypass path 204 on a first side of the sensor island 214 (above the island in the embodiment of FIG. 3A) and a second bypass path 205 on a second side of the sensor island 214 (below the island in the embodiment of FIG. 3A). The island 214 includes a sensor channel or opening 203 at the front of the island that leads to the sensor 100 positioned in the sensor receiving area 207 at the rear of the island. Gas that enters the sensor channel 203 will pass through the opening in the middle portion 34 of the optical bench assembly 3, then exit through a rear exhaust opening 216 in the island. The rear opening has exposed OBA 3, however the OBA 3 is not completely exposed since the opening has a size that prevents the airflow going through 205 to short-circuit inside the OBA 3 from the rear which will negatively affect sensor response time. The exhaust opening 216 can be aligned with or offset from the opening 38 of the OBA 3. In one embodiment, the island 214 can also have a rear wall 215 that is lower in height and doesn't reach the top of the body 250. Gas that doesn't enter the sensor channel 203 will pass around the sensor island 214 and exit at the exhaust choke point 212 where it meets up with gas exiting the bypass exhaust 211. At the exhaust choke point 212, the side walls gently taper outward to the exhaust 208, which can have a circular shape, as best shown in FIGS. 3C, 3D, 4.

In operation, breath measurements are achieved by bypassing most of the air in a way that the flow rate of the gas sample creates a pressure drop to pull the gas sample through the OBA 3 for fast response time. This type of arrangement is used because the sensor 100 has resistance due to the diffusion filters which are used to prevent contamination and water droplets from entering the sensor OBA 3. The gas sample enters the inlet side of the body 250 which could be a mouthpiece for the user's exhale. The geometry here can vary but the gas sample converges to the choke point 209 (though more than one can be provided) to increase the velocity and create a pressure drop. The bypass inlet 210 continues on a bypass route 206 and the bypass exhaust 211 serves as a bypass for the majority of the air flow.

The choke point 209 is necessary to correctly balance the air flow between the choke point 209 and the bypass 210, 206. The exhaust choke point 212 serves the same purpose, and they work together. When the person exhales or inhales, the pressure around the sensor does not change significantly, which is achieved by this configuration with the two choke points. The breath test can include inhaling and exhaling, which is why the design is symmetrical/reversible, though on inhale there is less restriction on how much air gets in the sensor measuring chamber because there is no danger of condensation.

Adjusting the cross-section size of this choke point 209 and bypass route 206 can adjust the performance of the system for a range of flow rates and desired pressure. The choke point 209 serves as the supply of air for the sensor. Once the sample passes the choke point 209 there can be a series of one or more baffles 202 that manipulate the flow to better bypass the sensor 100 with the majority of the air flow. A small opening 203 past the baffles 202 allows a path to the sensor 100 for the gas sample. The majority of the air flows via the bypass routes 206, 205 and 204 around the sensor 100. The three paths of the air around the sensor 203, 204, 205 converge with the bypass 210, 206, 211 ahead of an exhaust choke point 212 and the exhaust 208. The converging paths of air in the exhaust choke point 212 are critical to fast response time, not building pressure in the sensor 100 and condensation prevention.

The internal configuration of the body 250 brings the sensor approximately 0.1% of total exhaust in minimal amount of time and controls. A single choke point (and/or without baffles 202) was found to make noise (e.g., whistle) or condense water. If the air flow is not balanced correctly the following things may happen: (a) the design will be sensitive to input pressure and exhaled volume, and this device will be used by different people in different situations; (b) too much pressure change in the sensor chamber (we want to keep it at ambient pressure); (c) sensor response time will depend greatly on variances form individual to individual; (d) too much air passing through the sensor chamber causing thermal disturbances and condensation. The majority of the breath bypasses the actual sensor, the path to the sensor is around baffles, limited, and indirect.

Thus, the body 250 provides an obstructed path to the sensor 100. However, the gas sampling system 200 has a number of bypass routes 206, 204, 205 that overall provide low resistance to the breathing process so that the user can breathe through this system 200 while the measurements are being performed by the sensor 100. The choke points not only balance the flow but also provide required (controlled) resistance. The sensor assembly 100 that is depicted in FIG. 1 is assembled with the sampling system 200 in a way that the sensor OBA 3 fits in the area 207.

FIG. 4 illustrates how everything fits together in current embodiment with the sensor 100 mounted inside the gas sampling system with a simple screw and nut arrangement.

This system allows the user to breathe though this sampling system and at the same time create airflow conditions for consistent measurements. It also assures only minimal necessary amount of air reaches the sensor OBA location 207. This minimizes the amount of moisture entering the sensor OBA 3 and allows elimination of condensation with minimal electrical power on the heated window 5, or no extra electrical power at all in conditions when hydrophilic window can be sufficient. The amount of air reaching OBA is minimal, but allows real-time exhaled air dynamics. In addition, the sensor gas sampling system 100, 200 has a fast response time using a sensor measurement cell that is protected by diffusion filters 2 (FIG. 1). Solving the fast response time with diffusion hydrophobic filters on the sensor allows a long sensor lifetime without the need for replaceable parts or frequent periodic calibration.

The disclosure provides a low cost sampling system and sensor assembly that can be used in a wide ambient temperature range (10-40 degrees C.), low cost, fast response time, low power consumption, miniature (<pocket size) will enable a convenient portable breath measurement devices to be used comfortably by individuals rather than require to take breath samples at a hospital, or office where the more expensive and less portable equipment may exist. This allows more people, researchers, and individuals to have the ability to collect this data and learn to solve health related issues.

Long warm up time and high power is not necessary, which enables battery powered portable applications. Adding the heater element inside the OBA on the optical window prevents condensation in even lower temperatures. Due to very small size of the heated window both electrical power and warmup time of this design are still low and acceptable for portable battery powered application.

The mechanical design of the sampling system minimizes air flow through the sensor but achieves a response time <1 second. This is possible because the air is not being forced or pumped through the sensor 100, but rather the majority of the breath is bypassing the sensor. This breath bypass in combination with the choke points creates pressure differential to pull the gas sample through the sensor. This approach also does not build pressure in the sensor cell, so pressure will be approximately ambient pressure. This important because the accuracy of measurements depend on the gas pressure.

The disclosure provides a Nondispersive Infrared (NDIR) gas sensor and/or a sampling method and system that accurately samples human breath and measure dynamic of $CO_2$ concentration with time resolution of better than 0.3 seconds. Together they form innovative small size portable human breath analyzer developed to be used by regular consumers in a variety of environments.

The measurements are made directly in exhaled air. Human breath contains high level of humidity. The disclosure allows measuring $CO_2$ concentration directly in exhaled air with high moisture content accurately fast and without need for dehumidification. The disclosure eliminates a need for replaceable parts and can be used for breath analysis for years without need for service. In addition, the disclosure operates in a wide range of ambient temperature environments including outdoors and features of low power, small size and fast response time. The sensor sampling system can accurately measure the samples without condensation affecting the measurements in these environments.

This design can measure any gas that can be detected with an NDIR sensor, gases also known as greenhouse gases, this includes Water vapor (H2O), Carbon Monoxide (CO), Carbon Dioxide ($CO_2$), Hydrocarbons ($C_xH_y$), Hydrofluorocarbons, Refrigerants including Hydrofluorocarbons (HCFCs and HFCs) and Chlorofluorocarbons (CFCs). While NDIR $CO_2$ sensor is shown in one embodiment of this disclosure, the same approach can be used with other sensing technologies, whenever analyzed gas has high moisture content in a broad range of temperatures.

The gas measurement system 100, 200 allows direct measurements of $CO_2$ concentration in human breath, having fast response time (<1s) to changes in concentration and at the same time being insensitive to temperature gradients and condensation that may occur when a warm humid exhaled air sample enters a relatively cool sample chamber.

The system 100, 200 provides: (a) fast response time of measurement (100 milliseconds and less than 1 second) to allow breath dynamics measurements; (b) the warm up time after power on of the system is very short, nearly instant at <s without using the heater and <10 sec using the heater which make it attractive to use in battery powered applications; (c) insensitivity to high humidity content in exhaled air that could reach 100% RH; (d) operation under wide variety of temperature conditions making it usable in most practical environments indoors and outdoors, (e) low power allowing operation on small size batteries; and (f) no need for replaceable parts, water traps, Nafion tubing, or filters designed to remove water from the breath sample, or air pumps to control a stream sample. The design of the system results in accurate breath measurements in a wide ambient temperature range without the requirement of disposable pieces (often needed in main stream sample systems) and frequent calibrations.

A low-cost sampling system that can be used in a wide ambient temperature range, low cost, fast response time, low power consumption, miniature (<pocket size) will enable a convenient portable breath measurement devices to be used comfortably by individuals rather than require to take breath samples at a hospital, or office where the more expensive and less portable equipment may exist.

Analysis of exhaled breath measurements is a promising non-invasive way to monitor and diagnose individuals. An objective of the disclosure is to provide a human breath analyzer that can monitor $CO_2$ (and other gasses if necessary) that can be used by regular consumers similarly to other consumer products, in a variety of conditions without need for service or replicable parts and without special handling. This design is convenient and low cost so it can be used by individuals in the comfort of their residence, during their typical day, or when travelling.

$CO_2$ and CO and levels in breath can provide much information about the health of an individual. CO2 measurements for example in breath have known and unknown health applications that this sampling system and sensor may be useful in detecting. That includes but is not limited to metabolic functions, fat burn, digestion, efficiency of medicine, monitoring a patient's response to procedures or medicine, measurement of lung volume, measurement of airway dead-space, diagnosis and monitoring of respiratory diseases such as Asthma and chronic bronchitis (COPD).

CO measurements can be biomarkers for disease, oxidative stress, inflammation, and respiratory diseases. CO in breath may be useful as a tool to help individuals with smoking cessation, since a high level would be proportional to CO in the blood. Similarly, an individual that has been exposed to CO may have high CO in the breath and monitoring this over time is a noninvasive way to track recovery. Besides the absolute value of gases in exhaled breath, the shape of the breath response or dynamic changes within a single breath gives information about the subject. The fast response of the sensor allows the breath profile to be accurately measured. The shape of the CO2 on exhale is gives much information about the person under test.

It will be recognized that the geometry of the sampling system of the present disclosure can be in many forms. One important feature about the design is that the vast majority of the sample gas bypasses the sensor and the baffles 202, channels 205 and 204, passage 203 and choke point 211 are tuned to provide necessary air flow through the sensor area 207 while making it not sensitive to the user individual airflow variations. These ratios can be adjusted based on flow rates and application response time requirements. Thus, for example, heaters can be placed in places other than the window in the optical assembly, in practice this is what is being done in commercially available products today.

It is further noted that the description and claims use several geometric or relational terms, such as linear, curved, elongated, circular, oblong, tapered, parallel, perpendicular, transverse, planar, and flat. In addition, the description and claims use several directional or positioning terms and the like, such as front, rear, leading, trailing, above, below, top, bottom, side, left, right, up, down, inner, outer, distal, and proximal. Those terms are merely for convenience to facilitate the description based on the embodiments shown in the figures. Those terms are not intended to limit the disclosure. Thus, it should be recognized that the disclosure can be described in other ways without those geometric, relational, directional or positioning terms. In addition, the geometric or relational terms may not be exact. For instance, walls may not be exactly perpendicular or parallel to one another but still be considered to be substantially perpendicular or parallel because of, for example, roughness of surfaces, tolerances allowed in manufacturing, etc. And, other suitable geometries and relationships can be provided without departing from the spirit and scope of the disclosure.

The foregoing description and drawings should be considered as illustrative only of the principles of the disclosure. The disclosure may be configured in a variety of shapes and sizes and is not intended to be limited by the preferred embodiment. Numerous applications of the disclosure will readily occur to those skilled in the art. Therefore, it is not desired to limit the disclosure to the specific examples disclosed or the exact construction and operation shown and described. Rather, all suitable modifications and equivalents may be resorted to, falling within the scope of the disclosure.

The invention claimed is:

1. A gas sensor comprising:
a printed circuit board;
an optical detector on the printed circuit board;
a support assembly arranged over the optical detector and attached to the printed circuit board, the support assembly comprising:
a base portion enclosing the optical detector on the printed circuit board;
a middle portion with at least one opening and a sample chamber whereby gas enters the sample chamber through the at least one opening; and
a top portion;
an optical source arranged at the top portion of the support assembly, wherein optical radiation is directed from the optical source through the sample chamber to the optical detector;
a window arranged in the support assembly and positioned over the optical detector; and
a heating element operably connected to the window,
wherein the sample chamber is defined between the optical source and the window and
wherein the window is between the optical detector and the sample chamber and
wherein the window is in contact with the optical detector.

2. The gas sensor of claim 1, further comprising a filter covering the at least one opening to filter a gas entering the sample chamber.

3. The gas sensor of claim 1, wherein said window is enclosed by the base portion of the support assembly.

4. The gas sensor of claim 1, wherein said window has a hydrophilic or hydrophobic coating.

5. The gas sensor of claim 1, wherein said heating element is mounted to said window.

6. The gas sensor of claim 1, wherein the optical detector is an infrared detector and the optical source is an infrared source.

7. The gas sensor of claim 1, wherein the heating element is mounted to a surface of the window and arranged within the sample chamber.

8. The gas sensor of claim 1, wherein the heating element is mounted to a surface of the window opposite the sample chamber.

9. The gas sensor of claim 1, further comprising a seal arranged between the window and the base of the support assembly, the seal configured to sealing engage between the window and the base to fluidly separate the sample chamber and the optical detector and isolate the optical detector from the sample chamber.

10. The gas sensor of claim 1, further comprising a temperature sensor configured to monitor a temperature of said window and a microprocessor configured to cause activation of said heating element in response to the monitored temperature.

11. The gas sensor of claim 10, wherein the temperature sensor is mounted to said window on a same side of the window as the heating element.

12. The gas sensor of claim 1, wherein the window is attached to the printed circuit board by one or more fasteners.

13. The gas sensor of claim 12, wherein the one or more fasteners are conductive pins.

14. A gas sensor comprising:
a light detector on a printed circuit board;
a support structure attached to the printed circuit board and enclosing said light detector;
a window positioned in said support structure, wherein the light detector is between the window and the printed circuit board;
a light source mounted to said support structure, the light source aligned with said window and said light detector, the light source configured to direct light from said light source to said light detector through a sample chamber defined by the support structure and through said window; and
a heating element operably connected to said window,
wherein the sample chamber is defined between the light source and the window and
wherein the window is between the light source and the sample chamber and wherein the window is in contact with the optical detector.

15. The gas sensor of claim 14, wherein the sample chamber is configured to receive a gas to be tested.

16. The gas sensor of claim 14, further comprising a filter arranged to cover an opening to the sample chamber and filter a gas entering the sample chamber.

17. The gas sensor of claim 14, wherein said light source comprises an infrared light source and said light detector comprises an infrared light detector.

18. The gas sensor of claim 14, wherein said heating element is mounted to said window.

19. The gas sensor of claim 14, further comprising a temperature sensor configured to monitor a temperature of said window and a microprocessor configured to cause activation of said heating element in response to the monitored temperature.

20. A gas sensor comprising:
- a light detector on a printed circuit board;
- a support structure attached to the printed circuit board and enclosing said light detector;
- a window positioned in said support structure, wherein the light detector is between the window and the printed circuit board;
- a light source mounted to said support structure, the light source aligned with said window and said light detector, the light source configured to direct light from said light source to said light detector through a sample chamber defined by the support structure and through said window; and
- a heating element operably connected to said window,
- wherein the sample chamber is defined between the light source and the window and
  - wherein the window is between the light source and the sample chamber, and
- wherein the window is attached to the printed circuit board by one or more fasteners.

* * * * *